US009914692B2

(12) United States Patent
Chang et al.

(10) Patent No.: US 9,914,692 B2
(45) Date of Patent: Mar. 13, 2018

(54) PROCEDURE FOR THE PREPARATION OF 4-PHENYL BUTYRATE AND USES THEREOF

(71) Applicant: Horizon Therapeutics, LLC, Lake Forest, IL (US)

(72) Inventors: Huai-Chueh Chang, Tower Lakes, IL (US); Steven S. Pfeiffer, Camarillo, CA (US); Vasilios H. Iskos, Chicago, IL (US); Maki Uragami, Bethlehem, PA (US); Steven Weissman, Short Hills, NJ (US); Andrew Thompson, Mountainside, NJ (US)

(73) Assignee: Horizon Therapeutics, LLC, Lake Forest, IL (US)

( * ) Notice: Subject to any disclaimer, the term of this patent is extended or adjusted under 35 U.S.C. 154(b) by 0 days.

(21) Appl. No.: 15/164,126

(22) Filed: May 25, 2016

(65) Prior Publication Data

US 2017/0342018 A1  Nov. 30, 2017

(51) Int. Cl.
*A61K 31/235* (2006.01)
*C07C 69/616* (2006.01)
*C07C 51/29* (2006.01)
*C07C 57/30* (2006.01)
*C07C 67/14* (2006.01)

(52) U.S. Cl.
CPC ............ *C07C 69/616* (2013.01); *C07C 51/29* (2013.01); *C07C 57/30* (2013.01); *C07C 67/14* (2013.01)

(58) Field of Classification Search
CPC ....... C07C 69/616; C07C 67/14; C07C 51/29; C07C 57/30
USPC ................................. 514/532, 533
See application file for complete search history.

(56) References Cited

U.S. PATENT DOCUMENTS

| | | | |
|---|---|---|---|
| 3,686,238 | A | 8/1972 | Zaffaroni |
| 4,284,647 | A | 8/1981 | Brusilow et al. |
| 4,457,942 | A | 7/1984 | Brusilow |
| 5,654,333 | A | 8/1997 | Samid |
| 5,968,979 | A | 10/1999 | Brusilow |
| 6,060,510 | A | 5/2000 | Brusilow |
| 6,083,984 | A | 7/2000 | Brusilow |
| 6,219,567 | B1 | 4/2001 | Eggers et al. |
| 6,825,384 | B1 | 11/2004 | Prakash |
| 8,094,521 | B2 | 1/2012 | Levy |
| 8,404,215 | B1 | 3/2013 | Scharschmidt et al. |
| 8,642,012 | B2 | 2/2014 | Scharschmidt |
| 9,078,865 | B2 | 7/2015 | Lee |
| 9,095,559 | B2 | 8/2015 | Scharschmidt et al. |
| 9,254,278 | B2 | 2/2016 | Scharschmidt et al. |
| 9,289,406 | B2 | 3/2016 | Scharschmidt et al. |
| 9,326,966 | B2 | 5/2016 | Scharschmidt et al. |
| 2003/0195255 | A1 | 10/2003 | Summar |
| 2004/0229948 | A1 | 11/2004 | Summar et al. |
| 2005/0273359 | A1 | 12/2005 | Young |
| 2006/0135612 | A1 | 6/2006 | Ferrante |
| 2008/0119554 | A1 | 5/2008 | Jalan et al. |
| 2010/0008859 | A1 | 1/2010 | Scharschmidt |
| 2010/0016207 | A1 | 1/2010 | Wurtman et al. |
| 2012/0022157 | A1 | 1/2012 | Scharschmidt |
| 2012/0220661 | A1 | 8/2012 | Lee |
| 2013/0085179 | A1 | 4/2013 | Scharschmidt |
| 2013/0172543 | A1 | 7/2013 | Iwabuchi |
| 2013/0210914 | A1 | 8/2013 | Scharschmidt et al. |
| 2013/0281530 | A1 | 10/2013 | Scharschmidt et al. |
| 2014/0142186 | A1 | 5/2014 | Scharschmidt et al. |
| 2015/0094278 | A1 | 4/2015 | Scharschmidt et al. |
| 2015/0105469 | A1 | 4/2015 | Scharschmidt et al. |
| 2015/0335605 | A1 | 11/2015 | Scharschmidt et al. |
| 2016/0074356 | A1 | 3/2016 | Scharschmidt et al. |
| 2016/0081969 | A1 | 3/2016 | Scharschmidt et al. |
| 2016/0199332 | A1 | 7/2016 | Scharschmidt |
| 2016/0199333 | A1 | 7/2016 | Scharschmidt |
| 2016/0199334 | A1 | 7/2016 | Scharschmidt |
| 2016/0202240 | A1 | 7/2016 | Scharschmidt |

FOREIGN PATENT DOCUMENTS

| | | |
|---|---|---|
| CN | 1778963 | 5/2006 |
| CN | 103304402 A | 9/2013 |
| EP | 2607366 A1 | 6/2013 |
| IT | 1317073 B1 | 5/2003 |
| WO | WO1994/22494 | 10/1994 |
| WO | WO2005/053607 | 6/2005 |
| WO | WO2006/056794 | 6/2006 |
| WO | WO2007/005633 | 1/2007 |
| WO | WO2009/087474 | 7/2009 |
| WO | WO2009/134460 | 11/2009 |
| WO | WO 2009145323 A1 * 12/2009 ........... C07C 45/516 |

(Continued)

OTHER PUBLICATIONS

Shibuya et al., "Nitroxyl Radical/PhI(OAc)2: One-Pot Oxidative Cleavage of Vicinal Diols to (Di)Carboxylic Acids", 2012, Org. Lett., vol. 14, No. 19, pp. 5010-5013.*
Doi et al., "Development of an Azanoradamantane-Type Nitroxyl Radical Catalyst for Class-Selective Oxidation of Alcohols", 2015, The Journal of Organic Chemistry, 80(1), pp. 401-413.*
Ahrens, M. et al. (Jan. 2001). "Consensus Statement From a Conference for the Management of Patients With Urea Cycle Disorders." Supp. Journal of Pediatrics 138(1):S1-S5.
Ambrose, A.M. et al., "Further Studies on the Detoxification of Phenylacetic Acid", 101 J. Bio. Chem. 669-675 (1933).
Amodio, P., et al., "Detection of Minimal Hepatic Encephalopathy: Normalization and Optimization of the Psychometric Hepatic Encephalopathy Score. A Neuropsychological and Quantified EEG Study," J. Hepatol. 49:346-353 (2008).

(Continued)

Primary Examiner — My-Chau T. Tran
(74) Attorney, Agent, or Firm — Chris Marion

(57) ABSTRACT

Provided is a process for preparing 4-phenyl-1-butyric acid, comprising: reacting 4-phenyl-1-butanol with sodium chlorite, a nitroxyl radical catalyst and sodium hypochlorite in an organic solvent and a phosphate buffer; and quenching the reaction with sodium sulfite to produce 4-phenyl-1-butyric. Also provided is 4-phenyl-1-butyric acid prepared by such a process.

20 Claims, No Drawings

(56) References Cited

FOREIGN PATENT DOCUMENTS

| WO | WO2010/025303 | 3/2010 |
|---|---|---|
| WO | 2011011781 A1 | 1/2011 |
| WO | WO2012/028620 | 3/2012 |
| WO | WO2013/048558 | 4/2013 |
| WO | WO2013/158145 | 10/2013 |
| WO | WO2015/063659 | 5/2015 |

OTHER PUBLICATIONS

ANDA Notice Letter, Par Pharmaceutical, Inc. to Hyperion Therapeutics, inc.. Re: Glycerol Phenylbutyrate 1.1 gm/ml oral liquid; U.S. Pat. Nos. 8,404,215 and 8,642,012 Notice of Paragraph IV Certification Mar. 12, 2014, 27 pgs.

ANDA Notice Letter, Lupin Ltd. to Horizon Therapeutics, Inc.. Re: Notification of Invalidity, Unenforceability, and/or Noninfringement for U.S. Pat. Nos. 8,404,215 and 8,642,012 Pursuant to § 505(j)(2)(B)(ii) and (iv) of the Federal Food, Drug, and Cosmetic Act, Sep. 4, 2015, 57 pgs.

ANDA Notice Letter, Lupin Ltd. to Horizon Therapeutics, Inc.. Re: Notification of Invalidity, Unenforceability, and/or Noninfringement for U.S. Pat. No. 9,095,559 Pursuant to § 505(j)(2)(B)(ii) and (iv) of the Federal Food, Drug, and Cosmetic Act, Nov. 6, 2015, 30 pgs.

ANDA Notice Letter, Lupin Ltd. to Horizon Therapeutics, Inc.. Re: Notification of Invalidity, Unenforceability, and/or Noninfringement for U.S. Pat. No. 9,254,278 Pursuant to § 505(j)(2)(B)(ii) and (iv) of the Federal Food, Drug, and Cosmetic Act, Apr. 13, 2016, 42 pgs.

Bajaj, J. S., et al., "Review Article: The Design of Clinical Trials in Hepatic Encephalopathy—An International Society for Hepatic Encephalopathy and Nitrogen Metabolism (ISHEN) Consensus Statement," Aliment Pharmacol Ther. 33 (7):739-747 (2011).

Barsotti, "Measurement of Ammonia in Blood", 138 J. Pediatrics, S11-S20 (2001).

Batshaw, M.L. et al., "Treatment of Inborn Errors of Urea Synthesis: Activation of Alternative Pathways of Waste Nitrogen Synthesis and Excretion", 306 N. Engl. J. Med. 1387-1392 (1982).

Batshaw, M.L. et al., "New Approaches to the Diagnosis and Treatment of Inborn Errors of Urea Synthesis", 68 Pediatrics 290-297 (1981).

Batshaw, M.L. et al., "Treatment of Carbamyl Phosphate Synthetase Deficiency with Keto Analogues of Essential Amino Acids", 292 The New England J. Medicine, 1085-1090 (1975).

Batshaw, M.L. et al., "Treatment of Hyperammonemic Coma Caused by Inborn Errors of Urea Synthesis", 97 J. Pediatrics 893-900 (1980).

Batshaw, M.L., "Hyperammonemia," Current Problems in Pediatrics, vol. 14, Issue 11, p. 6-69 (1984).

Batshaw, M. L. et. al., "Alternative Pathway Therapy for Urea Cycle Disorder: Twenty Years Later", 138 J. Pediatrics S46-S55 (2001).

Berry, G. T. et al., "Long-Term Management of Patients with Urea Cycle Disorders", 138 J. Pediatrics S56-S61 (2001).

Blau, Duran, Blaskovics, Gibson (editors), Physician's Guide to the Laboratory Diagnosis of Metabolic Diseases, 261-276 (2d ed. 1996).

Blei, A. T., et al., "Hepatic Encephalopathy," Am. J. Gastroenterol. 96(7):1968-1976 (2001).

Brahe, C., et al., (2005) "Phenylbutyrate Increases SMN Gene Expression in Spinal Muscular Atrophy Patients," *Eur J Hum Genet* 13:256-259.

Brunetti-Pierri, N., et al., (2011) ""Phenylbutyrate Therapy for Maple Syrup Urine Disease"," Hum Mol Genet 20(4):631-640.

Brusilow, S.W. et al., "New Pathways of Nitrogen Excretion in Inborn Errors of Urea Synthesis", 2 Lancet 452-454 (1979).

Brusilow, S.W. et al., "Amino Acid Acylation: A Mechanism of Nitrogen Excretion in Inborn Errors of Urea Synthesis", 207 Science 659-661 (1980).

Brusilow, S.W., "Treatment of Episodic Hyperammonemia in Children With Inborn Errors of Urea Synthesis", 310 N. Engl. J. Med. 1630-1634 (1984).

Brusilow, S.W. Phenylacetylglutamine May Replace Urea as a Vehicle for Waste Nitrogen Excretion, Pediatric Research, vol. 29, No. 2, 147-150 (1991).

Brusilow, S.W. et al, "Treatment of Urea Cycle Disorders", in Treatment of Genetic Diseases 79-94 (R.J. Desnik. et al., eds.1991).

Brusilow, S.W. et al., "Restoration of Nitrogen Homeostasis in a Man with Ornithine Transcarbamylase Deficiency", 42 J. Metabolism 1336-1339 (1993).

Brusilow, S.W., "Protocols for Management of Intercurrent Hyperammonemia in Patients with Urea Cycle Disorders", FDA Application to Market a New Drug for Human Use or an Antibiotic Drug for Human Use, Fourteen pages (Amendment Dated Jul. 25, 1994).

Brusilow, S.W. et al., "Urea Cycle Disorders: Clinical Paradigm of Hyperammonemic Encephalopathy", 12 Progress in Liver Diseases 293-309 (1995).

Brusilow, S.W. et al., "Urea Cycle Enzymes", in the Metabolic and Molecular Bases of Inherited Diseases 1187-1232 (C.R. Scriver et al. eds. 1995).

Brusilow, S.W. et al., "Urea Cycle Disorders: Diagnosis, Pathophysiology, and Therapy", 43 Adv. Pediatr. 127-170 (1996).

Burlina, A.B. et al., "Long-Term Treatment with Sodium Phenylbutyrate in Ornithine Transcarbamylase-Deficient Patients", 72 Molecular Genetics and Metabolism 351-355 (2001).

Calloway, D.H. et al., "Sweat and Miscellaneous Nitrogen Losses in Human Balance Studies", 101 J. Nutrition 775-786 (1971).

Calloway, D.H. et al., "Variation in Endogenous Nitrogen Excretion and Dietary Nitrogen Utilization as Determinants of Human Protein Requirements", 101 J. Nutrition 205-216 (1971).

Camacho, L.H. et al., "Phase I Dose Escalation Clinical Trial of Phenylbutyrate Sodium Administered Twice Daily to Patients With Advanced Solid Tumors", 25 Invest. New Drugs 131-138 (2007, e-pub. Oct. 20, 2006).

Carducci, M., "Phenylbutyrate Induces Apoptosis in Human Prostate Cancer and Is More Potent Than Phenylacetate", 2 Clinical Cancer Research 379-387 (1996).

Carducci, M.A. et al., "A Phase I Clinical and Pharmacological Evaluation of Sodium Phenylbutyrate on an 120-h Infusion Schedule", 7 Clin. Cancer Res. 3047-3055 (2001).

Center for Drug Evaluation and Research, Clinical Pharmacology and Biopharmaceutics Review for New Drug Application No. 20-645 (Ammonul®) (2005), 34 pgs.

Center for Drug Evaluation and Research, Labeling for New Drug Application No. 20-645 (Ammonul®) (2005), 20 pgs.

Center for Drug Evaluation and Research, Medical Review for New Drug Application No. 20-645 (Ammonul®) (2005), 55 pgs.

Chang, C.-S.; Wu, P.-L. "Synthesis of triglycerides of phenylalkanoic acids by lipase-catalyzed esterification in a solvent-free system", J. Biotech. 127, 694-702 (2007).

Chang, C.-S.; Wu, P.-L. "Synthesis of triglycerides of phenybutyric acid by lipase", J. Molecular Catalysis B: Enzymatic 61, 117-122 (2009).

Chang, J.-G., et al., "Treatment of Spinal Muscular Atrophy by Sodium Butyrate", 98 PNAS USA 9808-9813 (2001).

Chen, Z. et al., "Tributyrin: A Prodrug of Butyric Acid for Potential Clinical Application in Differentiation Therapy", 54 Cancer Research 3494-3499 (1994).

Chung, Y.L., et al., (2000) "A Novel Approach for Nasopharyngeal Carcinoma Treatment Uese Phenylbutyrate as a Protein Kinase C Modulator: Implications for Radiosensitization and EBV-Targeted Therapy," Clin Cancer Res 6:1452-1458.

Clay, A. et. al, "Hyperammonemia in the ICU", 132 Chest 1368-1378 (2007).

ClinicalTrials.Gov/Archive View of NCT00551200 on Dec. 11, 2007, Dose-Escalation Safety Study of Glyceryl Tri (4-Phenylbutyrate)(GT4P) to Treat Urea Cycle Disorders, [accessed Oct. 5, 2009], 4 pages.

Collins, A.F. et al., "Oral Sodium Phenylbutyrate Therapy in Homozygous Beta Thalassemia: A Clinical Trial", 85 Blood 43-49 (1995).

(56) References Cited

OTHER PUBLICATIONS

Combined Search and Examination Report dated Oct. 9, 2009, for Great Britain Patent Application No. GB0915545.8, filed on Aug. 27, 2009, eight pages.
Combined Search and Examination Report dated Sep. 9, 2010, for Great Britain Patent Application No. 1013468.2, filed on Aug. 27, 2009, six pages.
'Complaint for Patent Infringement', *Hyperion Therapeutics, Inc.* v. *Par Pharmaceuticals, Inc.* Filed in U.S. District Court for the Eastern District of Texas, Apr. 23, 20141 14 pgs.
'Complaint for Patent Infringement', *Horizon Therapeutics, Inc.* v. *Lupin Ltd. and Lupin Pharmaceuticals Inc.* Filed in U.S. District Court for the District of New Jersey, Oct. 19, 2015, 104 pgs.
'Amended Complaint', *Horizon Therapeutics, Inc.* v. *Lupin Ltd. and Lupin Pharmaceuticals Inc.* Filed in U.S. District Court for the District of New Jersey, Apr. 6, 2016, 10 pgs.
Comte, B., et al., "Identification of Phenylbutyrylglutamine, A New Metabolite of Phenylbutyrate Metabolism in Humans", 37 J. Mass Spectrometry 581-590 (2002).
Conn, H. O., et al., "Liver Physiology and Disease: Comparison of Lactulose and Neomycin in the Treatment of Chronic Portal-Systemic Encephalopathy. A Double Blind Controlled Trial," Gastroenterology 72(4):573-583 (1977).
Cordoba, J., "New Assessment of Hepatic Encephalopathy," Journal of Hepatology 54: 1030-1040 (2011 ).
Cudkowicz (2009) "Phase 2 Study of Sodium Phenylbutyrate in ALS," Amyotrophic Lateral Sclerosis 10:99-106.
Darmaun, D. et al., "Phenylbutyrate-Induced Glutamine Depletion in Humans: Effect on Leucine Metabolism", 5 Am. J. of Physiology: Endocrinology and Metabolism E801-E807 (1998).
Darzens, G. et al.: "Preparation de quelques glycerides phenylaliphatiques et leur reduction en alcools . . . ", Comptes Rendus Hebdomadaires des Seances de L'Academie des Sciences., vol. 205, Oct. 18, 1937, pp. 682-684.
Deferrari, G. et al., "Brain Metabolism of Amino Acids and Ammonia in Patients with Chronic Renal Insufficiency", 20 Kidney International 505-510 (1981).
Diaz, G.A. et al., "Phase 3 Blinded, Randomized, Crossover Comparison of Sodium Phenylbutyrate (NaPBA) and Glycerol Phenylbutyrate (GPB): Ammonia (NH3) Control in Adults with Urea Cycle Disorders (UCDs)", 102 Mol. Genet. Metab. 276 (1981), Society of Inherited Metabolic Disease (SMID) Abstract, (2011).
Diaz G.A.et al, "Ammonia (NH3) control and improved neurocognitive outcome among urea cycle disorder (UCD) patients treated with glycerol phenylbutyrate (GPB)." Mol. Genet. Metab. 2012, 105, 311-312, SIMD Abstract 24.
Diaz, G. A., et al., "Ammonia Control and Neurocognitive Outcome Among Urea Cycle Disorder Patients Treated with Glycerol Phenylbutyrate," Hepatology 57(6):2171-2179 (2013).
Dixon, M. A. and Leonard, J.V., "Intercurrent Illness in Inborn Errors of Intermediary Metabolism, 67 Archives of Disease in Childhood", 1387-1391 (1992).
Dover, G. et al, "Induction of Fetal Hemoglobin Production in Subjects with Sickle Cell Anemia by Oral Sodium Phenylbutyrate", 84(1) Blood 339-343.
Endo, F. et al., "Clinical Manifestations of Inborn Errors of the Urea Cycle and Related Metabolic Disorders During Childhood", 134 J. Nutrition 1605S-1609S (2004).
Enns, G. M., et al., "Survival After Treatment with Phenylacetate and Benzoate for Urea-Cycle Disorders", 356 N. Eng. J. Med. 2282-2292 (2007).
European Medicines Agency, Annex I: Summary of Product Characteristics for Ammonaps, 1-33.
European Medicines Agency, European Public Assessment Report: Summary for the Public for Ammonaps (2009), 2 pgs.
European Medicines Agency, Scientific Discussion for Ammonaps (2005), 12 pgs.
European Medicines Agency, Scientific Discussion for Carbaglu (2004), 19 pgs.

European Patent Office, Extended European Search Report for EP09739263 completed Nov. 2, 2011, 6 pgs.
European Patent Office, International Search Report and Written Opinion for PCT/US2009/055256 completed Dec. 18, 2009 and dated Dec. 30, 2009, 13 pgs.
Examination Report dated Feb. 5, 2010, for United Kingdom Patent Application No. GB0915545.8, filed on Aug. 27, 2009, two pages.
Examination Report dated May 11, 2010, for United Kingdom Patent Application No. GB0915545.8, filed on Aug. 27, 2009, one page.
Examination Report dated Oct. 27, 2010, for United Kingdom Patent Application No. GB0915545.8, filed on Aug. 27, 2009, two pages.
Examination Report for British Patent Application No. GB1013468.2 dated Oct. 28, 2011, 2 pgs.
FDA Label for Ammonul®, sixteen pages. (Feb. 2005).
FDA Label for Buphenyl, six pages.
FDA Buphenyl® (Sodium Phenylbutyrate) Label, nine pages. (Aug. 2003).
FDA Label for Carbaglu, seven pages. (Mar. 2010).
Feillet, F. and Leonard, J.V., "Alternative Pathway Therapy for Urea Cycle Disorders", 21 J. Inher. Metab. Dis. 101-111 (1998).
Feoli-Fonseca, M. L., "Sodium Benzoate Therapy in Children with Inborn Errors of Urea Synthesis: Effect on Carnitine Metabolism and Ammonia Nitrogen Removal", 57 Biochemical and Molecular Medicine 31-36 (1996).
Ferenci, P., et al., "Hepatic Encephalopathy-Definition, Nomenclature, Diagnosis, and Quantification: Final Report of the Working Party at the 11th World Congresses of Gastroenterology, Vienna, 1998," Hepatology 35:716-721 (2002).
Fernandes, Saudubray, Berghe (editors), "Inborn Metabolic Diseases Diagnosis and Treatment", 219-222 (3d ed. 2000).
Gargosky, S. "Improved Survival of Neonates Following Administration of Ammonul® (Sodium Phenyl acetate & Sodium Benzoate) 10% 110% Injection", SSIEM Poster, six pages (Aug. 2, 2005).
Gargosky, S. et al., "Results of a Twenty-two Year Clinical Trial: Acute, Adjunctive Pharmacological Treatment of Hyperammonemic Episodes in Patients with Deficiencies in Enzymes of the Urea Cycle", poster, Ucyclyd Pharma, Inc., one page (Oct. 14, 2005).
Gargosky, S., "High Ammonia Levels Are Associated With Increased Mortality and Coma", Ucyclyd Pharma, Inc., one page (2006).
Geraghty, M.T. and Brusilow, S.W., Disorders of the Urea Cycle, in Liver Disease in Children 827-842 (F.J. Suchy et al., eds. 2001).
Ghabril, M. et al., Glycerol Phenylbutyrate (GPB) Administration in Patients with Cirrhosis and Episodic Hepatic Encephalopathy (HE), accepted for presentation at Digestive Disease Week (2012), 1 pg.
Ghabril, M. et al., "Glycerol Phenylbutyrate in Patients with Cirrhosis and Episodic Hepatic Encephalopathy: A Pilot Study of Safety and Effect on Venous Ammonia Concentration," Clinical Pharmacology in Drug Development 2(3): 278-284 (2013).
Gilbert, J. et al., "A Phase I Dose Escalation and Bioavailability Study of Oral Sodium Phenylbutyrate in Patients with Refractory Solid Tumor Malignancies", 7 Clin. Cancer Research 2292-2300 (2001).
Gore, S. et al., "Impact or the Putative Differentiating Agent Sodium Phenylbutyrate on Myelodysplastic Syndromes and Acute Myeloid Leukemia", 7 Clin. Cancer Res. 2330-2339 (2001).
Gropman, A.L. et al., "Neurological Implications of Urea Cycle Disorders", 30 J. Inherit Metab Dis. 865-879 (2007).
Gropman, A. L. et al., 1H MRS Allows Brain Phenotype Differentiation in Sisters with Late Onset Ornithine Transcarbamylase Deficiency (OTCD) and Discordant Clinical Presentations, 94 Mol. Genet. Metab. 52-60 (2008).
Gropman, A.L. et al., 1H MRS Identifies Symptomatic and Asymptomatic Subjects With Partial Ornithine Transcarbamylase Deficiency, 95 Mol. Genet. Metab. 21-30 (Sep.-Oct. 2008, e-pub. Jul. 26, 2008).
Gropman, A. (2010) "Brain Imaging in Urea Cycle Disorders," Mol Genet Metab 100:S20-S30.

(56) References Cited

OTHER PUBLICATIONS

Hassanein, T. I., et al., "Randomized Controlled Study of Extracorporeal Albumin Dialysis for Hepatic Encephalopathy in Advanced Cirrhosis," Hepatology 46:1853-1862 (2007).
Hassanein, T. I., et al., "Introduction to the Hepatic Encephalopathy Scoring Algorithm (HESA)," Dig. Dis. Sci. 53:529-538 (2008).
Hassanein, T., et al., "Performance of the Hepatic Encephalopathy Scoring Algorithm in a Clinical Trial of Patients With Cirrhosis and Severe Hepatic Encephalopathy," Am. J. Gastroenterol. 104:1392-1400 (2009).
Hines, P., et al., (2008) "Pulsed-Dosing with Oral Sodium Phenylbutyrate Increases Hemoglobin F in a Patient with Sickle Cell Anemia," Pediatr Blood Cancer 50:357-359.
Hogarth, P., et al., (2007) "Sodium Phenylbutyrate in Huntington's Disease: A Dose-Finding Study," Mov Disord 22(13):1962-1964.
Honda, S. et al., "Successful Treatment of Severe Hyperammonemia Using Sodium Phenylacetate Power Prepared in Hospital Pharmacy", 25 Biol. Pharm. Bull. 1244-1246 (2002).
Huang, H.H., et al., (2012) "Cannabinoid Receptor 2 Agonist Ameliorates Mesenteric Angiogenesis and Portosystemic Collaterals in Cirrhotic Rats," Hepatology 56:248-258.
Hyperion Therapeutics. "Hyperion Therapeutics Announces Enrollment of First Patient in Phase 1/2 Clinical Trial of GT4P in Patients with Urea Cycle Disorders" Announcement, 1 page (Oct. 23, 2007).
Hyperion Therapeutics. (Jun. 2, 2009.) Hyperion Therapeutics Announces Results of Phase I Study in Patients with Liver Cirrhosis, located at <http://www.hyperiontx.com/press/release/pr-1243891161>, last visited on Apr. 27, 2011, three pages.
Hyperion Therapeutics. (Mar. 30, 2009).,Hyperion Therapeutics Announces Results for Phase II Study in Urea Cycle Disorders, located at <http://www.hyperiontx.com/press/release/pr1238518388,> last visited on Apr. 27, 2011, three pages.
Hyperion Therapeutics. "Hyperion Therapeutics Announces Presentation of Long Term Data on Ammonia Control in Pediatric Patients Treated with Ravicti® at the 12$^{th}$ International Congress of Inborn Errors of Metabolism and the Urea Cycle Disorder Satellite Symposium", Press Release, Sep. 3, 2013.
International Preliminary Report on Patentability dated Mar. 1, 2011, for PCT Application No. PCT/US2009/030362, filed on Jan. 7, 2009, seven pages.
International Preliminary Report on Patentability dated Mar. 1, 2011, for PCT Application No. PCT/US2009/055256, filed on Aug. 27, 2009, six pages.
International Search Report and Written Opinion for PCT/US09/30362, dated Mar. 2, 2009, 8 pages.
International Search Report and Written Opinion for PCT/US2009/055256, dated Dec. 30, 2009, 13 pages.
International Preliminary Report on Patentability (Ch I) for PCT/US2012/028620 completed Jun. 4, 2012 and dated Apr. 10, 2014, 7 pgs.
International Preliminary Report on Patentability (Ch II) for PCT/US2012/028620, completed Aug. 22, 2013 and dated Sep. 4, 2013, 16 pgs.
Inter Partes Review of U.S. Pat. No. 8,404,215, 218 pgs, Apr. 29, 2015.
Inter Partes Review of U.S. Pat. No. 8,642,012, 186 pgs, Apr. 29, 2015.
James, M.O. et al., "The Conjugation or Phenylacetic Acid in Man, Sub-Human Primates and Some Other Non-Primates Species", 182 Proc. R. Soc. London 25-35 (1972).
John, B.A. et al., "The Disposition of HPN-100, A Novel Pharmaceutical Under Development for Potential Treatment of Hyperammonemia, in Cynomolgus Monkeys", ACMG 2009 ADME, poster, two pages (Mar. 2009).
John, Ba et al. (Mar. 2009). "The Disposition of HPN-100, A Novel Pharmaceutical Under Development for Potential Treatment of Hyperammonemia, in Cynomologus Monkeys," abstract presented at ACMG 2009, one page.
Kasumov T., et al., "New Secondary Metabolites of Phenylbutyrate in Humans and Rats", 32 Drug Metabolism and Disposition 10-19 (2004).
Khungar, V. et al., "Management of Overt Hepatic Encephalopathy," Clin. Liver Dis. 16 (2012), 73-89.
Kleppe, S. et al., "Urea Cycle Disorders", 5 Current Treatment Options in Neurology 309-319 (2003).
Kubota, K. and Ishizaki, T., Dose-Dependent Pharmacokinetics of Benzoic Acid Following Oral Administration of Sodium Benzoate to Humans, 41 Eur. J. Clin. Pharmacol. 363-368 (1991).
Lea et al., "Butyramide and Monobutyrin: Growth Inhibitory and Differentiating Agents", Anticancer Res., 13: 145-150 (1993).
Lee, B. and Goss, J., "Long-Term Correction of Urea Cycle Disorders", 138 J. Pediatrics S62-S71 (2001).
Lee, B. et al., "Considerations in the Difficult-to-Manage Urea Cycle Disorder Patient", 21 Crit. Care Clin. S19-S25 (2005).
Lee, B. et al. (Aug. 2009). "Dosing and Therapeutic Monitoring of Ammonia Scavenging Drugs and Urinary Phenylacetylglutamine (PAGN) as a Biomarker; Lessons From a Phase 2 Comparison of a Novel Ammonia Scavenging Agent With Sodium Phenylbutyrate (NaPBA)," abstract presented at ICIEM 2009, San Diego, CA, one page.
Lee, B. et al., "Dosing and Therapeutic Monitoring of Ammonia Scavenging Drugs and Urinary Phenylacetylglutamine (PAGN) as a Biomarker: Lessons From a Phase 2 Comparison of a Novel Ammonia Scavenging Agent with Sodium Phenylbutyrate (NAPBA)", presented at ICIEM 2009, San Diego, CA, poster, one page (Aug. 2009).
Lee, B. et al., "Phase 2 Study of a Novel Ammonia Scavenging Agent in Adults With Urea Cycle Disorders (UCDs)", abstract presented at ACMG 2009, one page (Mar. 2009).
Lee, B. et al., "Phase 2 Study of a Novel Ammonia Scavenging Agent in Adults with Urea Cycle Disorders (UCDs)", presented at ACMG 2009, seventeen pages (Mar. 2009).
Lee, B. et al., "Preliminary Data on Adult Patients with Urea Cycle Disorders (UCD) in an Open-Label, Switch-Over, Dose-Escalation Study Comparing a New Ammonia Scavenger, Glyceryl Tri (4-Phenylbutyrate) [HPN-100], to Buphenyl® (Sodium Phenylbutyrate [PBA])", abstract presented at SSIEM 2008, Lisbon, Portugal, one page. (Aug. 2008).
Lee, B. et al., "Preliminary Data on Adult Patients with Urea Cycle Disorders (UCD) in an Open-Label, Switch-Over, Dose Escalation Study Comparing a New Ammonia Scavenger, Glyceryl Tri (4-Phenylbutyrate) [HPN-100], to Buphenyl® (Sodium Phenylbutyrate [PBA])", presented at SSIEM 2008, Lisbon, Portugal, Poster, one page (Sep. 2008).
Lee, B., et al., "Preliminary Data on Adult Patients with Urea Cycle Disorders (UCD) in an Open-Label, Switch-Over, Dose-Escalation Study Comparing a New Ammonia Scavenger, Glyceryl Tri(4-Phenylbutyrate) (HPN-100), to Buphenyl (Sodium Phenylbutyrate [PBA])", 31 J. Inherit. Metab. Dis. 91 (2008).
Lee, B., et al., Phase 2 Comparison of a Novel Ammonia Scavenging Agent with Sodium Phenylbutyrate in Patients with Urea Cycle Disorders: Safety, Pharmacokinetics and Ammonia Control, 100 Mol. Genet. Metab. 221-228 (2010).
Lee, B., et al., "Optimizing Ammonia (NH3) Control in Urea Cycle Disorder (UCD) Patients: A Predictive Model," Oral Abstract Platform Presentations, Biochemical Genetics, Phoenix, AZ, Mar. 22, 2013, 2 pgs.
Lee, B. et al., "Blood ammonia and glutamine as predictors of hyperammonemic crises in patients with urea cycle disorder", Genetics Med. 17 (2015), 561-568.
Leonard, J.V., "Urea Cycle Disorders", 7 Semin. Nenatol. 27-35 (2002).
Levin, B. et al. "Hyperammonaemia: A Variant Type of Deficiency of Ornithinine Transcarbamylase." Arch. Dis. Childhd. 1969, 44, 162-169.
Lewis, H.B., "Studies in the Synthesis of Hippuric Acid in the Animal Organism. II. The Synthesis and Rate of Elimination of Hippuric Acid After Benzoate Ingestion in Man", 18 J. Biol. Chem. 225-231 (1914).
Liang, K.Y., et al., "Longitudinal Data Analysis Using Generalized Linear Models", 73 Biometrika 13-22 (1986).

(56) References Cited

OTHER PUBLICATIONS

Lichter-Konecki, U., et al., "Ammonia Control in Children with Urea Cycle Disorders (UCDs); Phase 2 Comparison of Sodium Phenylbutyrate and Glycerol Phenylbutyrate", 103 Mol. Genet. Metab. 323-329 (2011).
MacArthur, R. B., et al., "Pharmacokinetics of Sodium Phenylacetate and Sodium Benzoate Following Intravenous Administration as Both a Bolus and Continuous Infusion to Healthy Adult Volunteers", 81 Mol. Genet. Metab. S67-S73 (2004).
Maestri, N.E., et al., "Prospective treatment of urea cycle disorders", J Paediatr 1991;119:923-928.
Maestri, N.E. et al., "Plasma Glutamine Concentration: A Guide in the Management of Urea Cycle Disorders", 121 J. Pediatrics 259-261 (1992).
Maestri, N.E., et al., "Long-Term Survival of Patients with Argininosuccinate Synthetase Deficiency", 127 J. Pediatrics 929-935 (1993).
Maestri, N.E., "Long-Term Treatment of Girls with Ornithine Transcarbamylase Deficiency", 355 N. Engl. J. Med. 855-859 (1996).
Majeed, K., "Hyperammonemia", eMedicine.com (Dec. 2001), 12 pgs.
Mansour, A. et al., "Abdominal Operations in Patients with Cirrhosis: Still a Major Surgical Challenge", 122 Surgery 730 (1997) (Abstract Only), 1 pg.
Marini, J.C. et al., "Phenylbutyrate Improves Nitrogen Disposal via an Alternative Pathway without Eliciting an Increase in Protein Breakdown and Catabolism in Control and Ornithine Transcarbamylase-Deficient Patients", 93 Am. J. Clin. Nutr. 1248-1254 (2011).
Matsuda, I., "Hyperammonemia in Pediatric Clinics: A Review of Ornithine Transcarbamylase Deficiency (OTCD) Based on our Case Studies", 47 JMAJ 160-165 (2004).
McGuire, B. et al., "Pharmacokinetic (PK) Safety Study of Sodium Phenylacetate and Sodium Benzoate Administered to Subjects with Hepatic Impairment", abstract of The 13th International Symposium, Abano (Padova), Italy, Apr. 28-May 1, 2008, two pages (Apr. 2008).
McGuire, B. et al., "Pharmacokinetic Safety Study of Sodium Phenylacetate and Sodium Benzoate Administered to Subjects With Hepatic Impairments", 28 Liver International 743 (2008) (Abstract Only), 1 page.
McGuire, B.M. et al., "Pharmacokinetic (PK) and Safety Analyses of a Novel Ammonia—Reducing Agent in Healthy Adults and Patients with Cirrhosis", Hyperion Therapeutics, poster, one page (2009).
McGuire, B. M., et al., "Pharmacology and Safety of Glycerol Phenylbutyrate in Healthy Adults and Adults with Cirrhosis", 51 Hepatol. 2077-2085 (2010).
McQuade, P.S., "Analysis and the Effects of Some Drugs on the Metabolism of Phenylethylamine and Phenylacetic Acid", 8 Neuropsychopharmacol. Bio. Psychiat.607-614 (1984).
Mercuri, E., et al., (2004) "Pilot Trial of Phenylbutyrate in Spinal Muscular Atrophy," Neuromuscul Disord 14:130-135.
Mizutani, N. et al., "Hyperargininemia: Clinical Course and Treatment with Sodium Benzoate and Phenylacetic Acid", 5 Brain and Development 555-563 (1983).
Mokhtarani, M., et al., (2012) "Elevated Phenylacetic Acid (PAA) Levels Appear Linked to Neurological Adverse Events in Healthy Adults But Not in Urea Cycle Disorder (UCD) Patients," Mol Genet Metab 105:Abstract Only.
Mokhtarani, M., et al., (2013) "Elevated Phenylacetic Acid Levels Do Not Correlate with Adverse Events in Patients with Urea Cycle Disorders o rHepatic Encephalopathy and Can Be Predicted Based on the Plasma PAA to PAGN Ratio," Mol Genet Metab 110(4), 21 pgs.
Mokhtarani et al., (2012) "Urinary phenylacetylglutamine appears to be a more useful marker than metabolite blood levels for therapeutic monitoring of phenylacetic acid (PAA) prodrugs." Mol Genet Metab 105, 341-342, SIMD Abstract 78.
Mokhtarani, M., et al., (2012) "Urinary Phenylacetylglutamine as Dosing Biomarker for Patients with Urea Cycle Disorders," Mol Genet Metab 107(3), 16 pgs.
Moldave, K., et al., (1957) "Synthesis of Phenylacetylglutamine by Human Tissue," J. Biol. Chem. 229:463-476.
Monteleone, JPR, et al., (2012) "Population pk Analysis of Glycerol Phenylbutyrate (GPB) and Sodium Phenylbutyrate(NAPBA) in Adult and Pediatric Patients with Urea Cycle Discarders," Mol Genet Metab 105:Abstract Only.
Monteleone, JPR, et al., (2013) "Population Pharmacokinetic Modeling and Dosing Simulations of Nitrogen-Scavenging Compounds: Disposition of Glycerol Phenylbutyrate and Sodium Phenylbutyrate in Adult and Pediatric Patients with Urea Cycle Disorders," J. Clin. Pharmacol. 53(7): 699-710.
Munoz, S. J., "Hepatic Encephalopathy," Med. Clin. N. Am. 92:795-812 (2008).
Nassogne, M.C., "Urea Cycle Defects: Management and Outcome", 28 J. Inherit. Metab. Dis. 407 (2005), 407-414.
Newmark, H. L. and Young, W. C., "Butyrate and Phenylacetate as Differentiating Agents: Practical Problems and Opportunities", 22 J. Cellular Biochemistry 247-253 (1995).
Ong, J. P., et al., (2003) "Correlation Between Ammonia Levels and the Severity of Hepatic Encephalopathy," Am. J. Med. 114:188-193.
Ortiz, M., et al., "Development of a Clinical Hepatic Encephalopathy Staging Scale," Aliment Pharmacol Ther 26:859-867 (2007).
Par Pharmaceutical, Inc.'s Initial Invalidity Contentions and Non-Infringement Contentions for U.S. Pat. Nos. 8,404,215 and 8,642,012, Nov. 13, 2014, 93. Pgs.
Parsons-Smith, B. G., et al., "The Electroencephalograph in Liver Disease," Lancet 273:867-871 (1957).
Perrine, S. P., (2008) "Fetal Globin Stimulant Therapies in the Beta-Hemoglobinopathies: Principles and Current Potential," Pediatr Ann 37(5):339-346.
Phuphanich, S. et al., "Oral Sodium Phenylbutyrate in Patients with Recurrent Malignant Gliomas: A Dose Escalation and Pharmacologic Study", Neuro-Oncology 177-182 (2005).
Piscitelli, S.C. et al., "Disposition of Phenylbutyrate and its Metabolites, Phenylacetate and Phenylacetylglutamine", 35 J. Clin. Pharmacology 368-373 (1995).
Praphanproj, V. et al., "Three Cases of Intravenous Sodium Benzoate and Sodium Phenylacetate Toxicity Occurring in the Treatment of Acute Hyperammonemia," 23 J. Inherited Metabolic Disease 129-136 (2000).
Propst, A. et al., "Prognosis and Life Expectancy in Chronic Liver Disease", 40 Dig Dis Sci 1805 (1995) (Abstract Only), 1 pge.
Riley, T.R. et al., "Preventive Strategies in Chronic Liver Disease: Part Ii", Cirrhosis, 64 Am. Fam. Physician 1735 (2001). (Abstract Only), 1 pge.
Rockey, D. C., et al., "Randomized, Controlled, Double Blind Study of Glycerol Phenylbutyrate in Patients with Cirrhosis and Episodic Hepatic Encephalopathy," Hepatology 56:248(a) (2012), 1 pge.
Rudman, D., et al., "Maximal Rates of Excretion and Synthesis of Urea in Normal and Cirrhotic Subjects", 52 J. Clin. Invest. 2241-2249 (1973).
Ryu, H., et al., (2005) "Sodium Phenylbutyrate Prolongs Survival and Regulates Expression of Anti-Apoptotic Genes in Transgenic Amyotrophic Lateral Sclerosis Mice," J Neurochem 93:1087-1098.
Salam, M., et al., "Modified-Orientation Log to Assess Hepatic Encephalopathy," Aliment Pharmacol Ther. 35(8):913-920 (2012).
Scientific Discussion for Ammonaps, EMEA 2005, available at http://www.ema.europa.eu/docs/en_GB/document_library/EPAR_-_Scientific_Discussion/human/000219/WC500024748.pdf, 12 pgs.
Scottish Medicines Consortium, Carglumic Acid 200 mg Dispersible Tablets (Carbaglu®) No. 299/06 (Sep. 8, 2006), 5 pgs.
Seakins, J.W.T., "The Determination of Urinary Phenylacetylglutamine as Phenylacetic Acid: Studies on its Origin in Normal Subjects and Children with Cystic Fibrosis", 35 Clin. Chim. Acta. 121-131 (1971).
Search and Examination Report for British Patent Application No. GB 0915545.8, dated Oct. 8, 2009, 5 pages.

(56) References Cited

OTHER PUBLICATIONS

Seiki et al., "Homogenous Pharmaceutical Emulsions Containing Nonsteriodal Analogesics and Inflammation Inhibitors" Chemical Abstract, vol. 116, No. 46308, 1 pge.

Sherwin, C. et al., "The Maximum Production of Glutamine by the Human Body as Measured by the Output of Phenylacetylglutamine", 37 J. Biol. Chem. 113-119 (1919).

Shiple, G.J. et al., "Synthesis of Amino Acids in Animal Organisms. I. Synthesis of Glycocoll and Glutamine in the Human Organism", 44 J. Am. Chem. Soc. 618-624 (1922).

Simell, O., et al., "Waste Nitrogen Excretion Via Amino Acid Acylation: Benzoate and Phenylacetate in Lysinuric Protein Intolerance", 20 Pediatr. Res. 1117-1121 (1986).

Singh, "Consensus Statement from a Conference for the Management of Patients with Urea Cycle Disorders", 138 J. Pediatrics S1-S5 (2001).

Smith, W., et al., "Ammonia Control in Children Ages 2 Months through 5 Years with Urea Cycle Disorders: Comparison of Sodium Phenylbutyrate and Glycerol Phenylbutyrate," J Pediatr. 162(6):1228-1234.e1 (2013).

Stauch, et al., (1998) "Oral L-ornithine-L-aspartate therapy of chronic hepatic encephalopathy: results of a placebo-controlled double-blind study" J Hepatology 28(5):856-864.

Summar, M., "Current Strategies for the Management of Neonatal Urea Cycle Disorders", 138 J. Pediatrics S30-S39 (2001).

Summar, M. and Tuchman, M., "Proceedings of a Consensus Conference for the Management of Patients with Urea Cycle Disorders", 138 J. Pediatrics S6-S10 (2001).

Summar, M., "Urea Cycle Disorders Overview, Gene Reviews", www.genetests.org (Apr. 2003), 15 pgs.

Summar, M. et al., "Unmasked Adult-Onset Urea Cycle Disorders in the Critical Care Setting", 21 Crit. Care Clin. S1-S8 (2005).

Summar, M. et al., "Description and Outcomes of 316 Urea Cycle Patients From a 21-Year, Multicenter Study of Acute Hyperammonemic Episodes", Abstract, presented at Annual Symposium CCH-Congress Centre Hamburg, Sep. 4-7, 2007, GSSIEM 2007, two pages.

Summar, M.L. et al., "Diagnosis, Symptoms, Frequency and Mortality of 260 Patients with Urea Cycle Disorders From a 21-Year, Multicentre Study of Acute Hyperammonemic Episodes", 97 Acta Paediatr. 1420-1425 (Oct. 2008, e-pub. Jul. 17, 2008).

Sushma, S. et al., "Sodium Benzoate in the Treatment of Acute Hepatic Encephalopathy: A Randome Double-blind Trial," Hepatology, 16 (1992), 138-144.

Swedish Orphan International, "Urea Cycle Disorders an International Perspective", Poster, Symposium Swedish Orphan International, Barcelona, Spain, Jan. 12, 2007, one page.

Tanner, L. M., et al., "Nutrient Intake in Lysinuric Protein Intolerance", 30 J. Inherit. Metab. Dis. 716 (2007), 716-721.

The National Organization for Rare Disorders (2012). The Physician's Guide to Urea Cycle Disorders, at http://nordphysicianguides.org/wp-content/uploads/2012/02/NORD_Physician_Guide_to_Urea_Cycle_Disorders.pdf, 28 pgs.

Thompson, P. "Pharmacokinetics of phenyacetate administered as a 30-min infusion in children with refractory cancer", Cancer Chemother. Pharmacol. 2003, 52: 417-423.

Thibault, A., et al., "A Phase I and Pharmacokinetic Study of Intravenous Phenylacetate in Patients with Cancer", 54 Cancer Res. 1690-1694 (1994).

Thibault, A., et al., "Phase I Study of Phenylacetate Administered Twice Daily to Patients with Cancer", 75 Cancer 2932 (1995).

Todo, S. et al., "Orthotopic Liver Transplantation for Urea Cycle Enzyme Deficiency", 15 Hepatology 419-422 (1992).

Tuchman, M., and Yudkoff, M., "Blood Levels of Ammonia and Nitrogen Scavenging Amino Acids in Patients with Inherited Hyperammonemia", 66 Molecular Genetics and Metabolism 10-15 (1999).

Tuchman, M. et al., Cross-Sectional Multicenter Study of Patients With Urea Cycle Disorders in the United States, 94 Molec. Genetics Metab. 397-402 (2008, e-pub. Jun. 17, 2008).

UMass Memorial Medical Center, Lab Updates, "Measurement of Ammonia in Blood." Feb. 2007. Accessed at www.ummlabs.org/News/07Feb.pdf, 3 pgs.

United States Patent and Trademark Office, International Search Report and Written Opinion for PCT/US2009/030362, dated Mar. 2, 2009, 9 pgs.

United States Patent and Trademark Office, International Search Report and Written Opinion dated Jun. 20, 2012 for PCT/US2012/028620.

United States Patent and Trademark Office, International Search Report and Written Opinion for PCT/US2012/54673 dated Nov. 20, 2012, 8 pgs.

United States Patent and Trademark Office, International Search Report and Written Opinion for PCT/US2013/71333 dated Mar. 28, 2014, 9 pgs.

United States Patent and Trademark Office, International Search Report and Written Opinion dated Jan. 16, 2015 for PCT/US14/58489, 8 pgs.

United States Patent and Trademark Office, International Search Report and Written Opinion for PCT/US2014/060543 dated Jan. 23, 2015.

Vilstrup, H., et al., "Hepatic Encephalopathy in Chronic Liver Disease: 2014 Practice Guideline by the American Association for the Study of Liver Diseases and the European Association for the Study of the Liver," Hepatology 60 (2):715-735 (2014).

Walsh et al., Chemical Abstract vol. 112, No. 231744, 1990, 1 pge.

Walsh et al., The Journal of Biological Chemistry, vol. 265, No. 8, pp. 4374-4381 (1990), "sn-1,2-Diacylgylcerol Kinase of *Escherichia coli*".

Waterlow, J.C., The Partition of Nitrogen in the Urine of Malnourished Jamaican Infants, 12 Am. J. of Clin. Nutrition 235-240 (1963).

Welbourne, T. et al., "The Effect of Glutamine Administration on Urinary Ammonium Excretion in Normal Subjects and Patients with Renal Disease", 51 J. Clin. Investigation 1852-1860 (1972).

Wicken, B., "Problems in the Management of Urea Cycle Disorders", 81 Molecular Genetics and Metabolism 85 (2004).

Wilson, C.J., et al., "Plasma Glutamine and Ammonia Concentrations in Ornithine Carbamoyltransferase Deficiency and Citrullinaemia", 24 J. Inherited Metabolic Disease 691 (2001).

Wright, G., et al., "Management of Hepatic Encephalopathy", 2011 International Journal of Hepatology 1 (2011), 11 pgs.

Wright, P., Review: "Nitrogen Excretion: Three End Products, Many Physiological Roles", 198 J. Experimental Biology 273-281 (1995).

Xie, G., et al., (2012) "Role of Differentiation of Liver Sinusoidal Endothelial Cells in Progression and Regression of Hepatic Fibrosis in Rats," Gastroenterology 142:S918-927.

Yajima, et al. "Diurnal Fluctuations of Blood Ammonia Levels in Adult-Type Citrullinemia", 137 Tokohu J. Ex/ Med, 213-220 (1982).

Yu, Ryan and Potter, Murray, "Diagnosis of Urea Cycle Disorders in Adulthood: Late-Onset Carbamyl Phosphate Synthetase 1 Deficiency", 7 MUMJ 30-32 (2010).

Yudkoff, M. et al., "In Vivo Nitrogen Metabolism in Ornithine Transcarbamylase Deficiency", 98 J. Clin. Invest. 2167-2173 (1996).

Zeitlin, P., "Novel Pharmacologic Therapies for Cystic Fibrosis", 103 J. Clinical Investigation 447-452 (1999).

Zeitlin, P.L. et al., "Evidence of CFTR Function in Cystic Fibrosis After System Administration of 4-Phenylbutyrate", 6 Mol. Therapy 119-126 (2002).

"Program for SIMD annual meeting", Molecular Genetics and Metabolism, (Mar. 1, 2012), vol. 105, No. 3, doi:10.1016/j.ymgme.2012.01.004, ISSN 1096-7192, pp. 273-366, XP055202401.

Anonymous, "Application No. 20-645 Medical Review FDA", (Feb. 15, 2005), pp. 1-55, URL: http://www.accessdata.fda.gov/drugsatfda_docs/nda/2005/020645s000_MedR.pdf, (Mar. 22, 2016), XP055260195.

Chemical Abstracts, vol. 112, No. 25, Jun. 18, 1990, (Columbus, Ohio, USA), p. 270, Abstract No. 231744t, Walsh J.P., "SN-1,2-Diacylglycerol Kinase of *Escherichia coli*. Diacylglycerol Analogs Define Specificity and Mechanism"; & Journal of Biological Chemistry, 1990, 265(8), (Eng).

(56) References Cited

OTHER PUBLICATIONS

Complaint', *Horizon Therapeutics, Inc.* v. *Lupin Ltd. et al.*; U.S. District Court for the District of New Jersey; Civ. Action No. 1:16-cv-00438-RBK-JS; Filed Jul. 21, 2016.
Complaint', *Horizon Therapeutics, Inc.* v. *Par Pharmaceutical, Inc.*; U.S. District Court for the District of New Jersey; Civ. Action No. 1:16-cv-03910-RBK-JS; Filed Jun. 30, 2016.
Cordoba, J., "New assessment of hepatic encephalopathy.", Journal of Hepatology, (2011), vol. 54, p. 1030, 1032, 1038, XP028192163.
Examination Report for British Patent Application No. GB0915545.8 dated Oct. 27, 2010.
FDA Label for Carbagiu, seven pages. (Mar. 2010).
Inter Partes Review of U.S. Pat. No. 8,404,215 Petition Apr. 29, 2015.
Lizardi-Cervera, J. et al, 'Hepatic Encephalopathy: A Review', 2 Annals of Hepatology 122-120 (2003).
McGuire, B. et al. (2009) 'Pharmacokinetic (PK) and Safety Analyses of a Novel Ammonia-Reducing Agent in Healthy Adults and Patients with Cirrhosis,' abstract presented at DDW, two pages.
South San et al, 'Hyperion Therapeutics Announces Presentation of Long Term Data on Ammonia Control in Pediatric Patients Treated With Ravicti(R) at the 12th International Congress of Inborn Errors of Metabolism and the Urea Cycle Disorder Satellite Symposium', (Sep. 3, 2013) URL: http://files.shareholder.com/downloads/AMDA-1412CE/0x0x688110/4e684e9d-6c54-4963-a993-72c90f308802/HPTX_News_2013_9_3_General_Releases.pdf, (Mar. 21, 2016), XP055260208.
Fey, et al., "Silica-Supported TEMPO Catalysts: Synthesis and Application in the Anelli Oxidation of Alcohols," J. Org. Chem., 2001, 66 (24), pp. 8154-8159.
Zhao, et al., "Oxidation of Primary Alcohols to Carboxylic Acids with Sodium Chlorite Catalyzed by Tempo and Bleach," J. Org. Chem., 1999, 64 (7), pp. 2564-2566.
Uribe M et al., Hyperammonemic Hepatic Encypholopathy Treated with Sodium Benzoate, Final report of double blind evaluation, Instituto Nacional de la Nutricion, Mexico D.F., Hepatology, 1989, vol. 10, No. 4, p. 589. Illegible.
Koya, Toshinari et al., Poster Session, Liver P-397, A study of administration of granular preparations of branched chain amino acids during transcatheter arterial chemoembolisation for hepatocellular carcinoma, Department of Gastrointestinal Medicine, Anjo Kosei Hospital, 2017, p. A775.
Nagazumi Atsushi et al., Use experience of Monilac for hepatic encephalopathy, Journal of New Remedies & Clinics, vol. 24, No. 8, Aug. 1975, pp. 1271-1274 41-44.
Complaint', *Horizon Therapeutics, Inc.* v. *Lupin Ltd. et al.*; U.S. District Court for the District of New Jersey; Civ. Action No. 2:17-cv-05900-KM-MAH; Filed Aug. 8, 2017.
Complaint', *Horizon Therapeutics, Inc.* v. *Par Pharmaceutical, Inc.*; U.S. District Court for the District of New Jersey; Civ. Action No. 2:17-cv-05901-KM-MAH; Filed Aug. 8, 2017.
IPR2015-01117, Inter partes review of U.S. Pat. No. 8,642,012, Final written decision 35 U.S.C. § 318 and 37 C.F.R. § 42.73.
IPR2015-01127, Inter partes review of U.S. Pat. No. 8,404,215, Final written decision 35 U.S.C. § 318 and 37 C.F.R. § 42.73.
IPR2016-00283, Inter partes review of U.S. Pat. No. 8,642,012, Petition, pursuant to §§ 35 U.S.C. 311-319 and 37 C.F.R. § 42, Dec. 4, 2015.
IPR2016-00283, Inter partes review of U.S. Pat. No. 8,642,012, Final written decision 35 U.S.C. § 318 and 37 C.F.R. § 42.73.
IPR2016-00284, Inter partes review of U.S. Pat. No. 8,404,215, Petition, pursuant to §§ 35 U.S.C. 311-319 and 37 C.F.R. § 42, Dec. 4, 2015.
IPR2016-00284, Inter partes review of U.S. Pat. No. 8,404,215, Final written decision 35 U.S.C. § 318 and 37 C.F.R. § 42.73.
IPR2016-00829, Inter partes review of U.S. Pat. No. 9,095,559, Petition, pursuant to §§ 35 U.S.C. 311-319 and 37 C.F.R. § 42, Apr. 1, 2016.
IPR2016-00829, Inter partes review of U.S. Pat. No. 9,095,559, Patent owner response.
IPR2017-01159, Inter partes review of U.S. Pat. No. 9 9,254,278, Petition, pursuant to §§ 35 U.S.C. 311-319 and 37 C.F.R. § 42.
IPR2017-01159, Inter partes review of U.S. Pat. No. 9 9,254,278, Preliminary Patent Owner Response.
IPR2017-01160, Inter partes review of U.S. Pat. No. 9,326,966, Petition, pursuant to §§ 35 U.S.C. 311-319 and 37 C.F.R. § 42.
IPR2017-01160, Inter partes review of U.S. Pat. No. 9,326,966, Preliminary Patent Owner Response.
IPR2017-01767, Inter partes review of U.S. Pat. No. 9,254,278, Petition, pursuant to §§ 35 U.S.C. 311-319 and 37 C.F.R. § 42.
IPR2017-01768, Inter partes review of U.S. Pat. No. 9,095,559, Petition, pursuant to §§ 35 U.S.C. 311-319 and 37 C.F.R. § 42.
IPR2017-01769, Inter partes review of U.S. Pat. No. 9,326,966, Petition, pursuant to §§ 35 U.S.C. 311-319 and 37 C.F.R. § 42.

\* cited by examiner

PROCEDURE FOR THE PREPARATION OF 4-PHENYL BUTYRATE AND USES THEREOF

The oxidation of primary alcohols to carboxylic acids is a transformation of broad utility in synthetic chemistry. Commonly used methods include the use of chromium (VI) oxide in sulfuric acid, ruthenium (III) chloride with $H_5IO_6$ and Swern oxidation of the alcohol to the aldehyde, followed by oxidation of the aldehyde with $NaClO_2$. These methods suffer from disadvantages such as the disposal issues relating to the use of metals, and the generation of equimolar amounts of sulfides in the Swern procedure.

TEMPO, i.e., 2,2,6,6,-tetramethyl-1-piperdinyloxy, free radical, together with sodium hypochlorite (NaClO) also can be used for oxidation. A variant of the TEMPO procedure, a one-step procedure using sodium chlorite in the presence of a catalytic amount of TEMPO and sodium hypochlorite which reduces the epimerization of any α-chiral centers, has been described.

4-Phenyl-1-butyrate, which may be prepared by oxidation of 4-phenyl-1-butanol, is a useful intermediate for the preparation of glycerol phenylbutyrate (glycerol tri-[phenylbutyrate]; HPN-100). Glycerol phenylbutyrate is a nitrogen-scavenging drug for the treatment of nitrogen retention disorders such as urea cycle disorders and hepatic encephalopathy.

Provided is a process for the preparation of 4-phenyl-1-butyric acid comprising: oxidizing 4-phenyl-1-butanol with sodium chlorite, a nitroxyl radical catalyst, and sodium hypochlorite in an organic solvent and a phosphate buffer and quenching the reaction by the addition of sodium sulfite.

Also provided is 4-phenyl-1-butyric acid prepared by a process described herein.

Also provided is a process for converting 4-phenyl-1-butyric acid prepared as described herein to glycerol triphenylbutyrate comprising: converting 4-phenyl-1-butyric acid prepared by the process disclosed herein to 4-phenyl-1-butyryl chloride; and reacting the 4-phenyl-1-butyryl chloride with glycerol in an organic solvent in the presence of a suitable base.

Also provided is glycerol triphenylbutyrate prepared by a process described herein.

These and other aspects of the invention disclosed herein will be set forth in greater detail as the patent disclosure proceeds.

Provided is a process for the preparation of 4-phenyl-1-butyric acid comprising: reacting 4-phenyl-1-butanol with sodium chlorite, a nitroxyl radical catalyst, and sodium hypochlorite in an organic solvent and a phosphate buffer; and quenching the reaction with sodium sulfite to produce 4-phenyl-1-butyric acid.

In some embodiments, reacting 4-phenyl-1-butanol with sodium chlorite, a nitroxyl radical catalyst and sodium hypochlorite in an organic solvent and a phosphate buffer comprises sequentially adding sodium chlorite and sodium hypochlorite to a mixture of 4-phenyl-1-butanol and a nitroxyl radical catalyst in an organic solvent and a phosphate buffer.

In some embodiments, reacting 4-phenyl-1-butanol with sodium chlorite, a nitroxyl radical catalyst and sodium hypochlorite in an organic solvent and a phosphate buffer comprises dissolving 4-phenyl-1-butanol and a catalytic amount of a nitroxyl radical catalyst, together with a catalytic amount of sodium hypochlorite in the organic solvent to form a solution and then adding the phosphate buffer to the solution. In some embodiments, the dissolution is conducted at ambient temperature with stirring.

In some embodiments, reacting 4-phenyl-1-butanol with sodium chlorite, a nitroxyl radical catalyst, and sodium hypochlorite in an organic solvent and a phosphate buffer comprises adding an aqueous solution of sodium chlorite and a catalytic amount of sodium hypochlorite while maintaining the temperature of the reaction mixture at 20-25° C.

In some embodiments, the method further comprises adjusting the pH of the reaction mixture to about 9.8 with aqueous sodium hydroxide prior to quenching the reaction.

In some embodiments, the nitroxyl radical catalyst is chosen from a TEMPO catalyst and an AZADO catalyst or a mixture thereof.

In some embodiments, the TEMPO catalyst is chosen from (2,2,6,6-tetramethyl-1-piperidinyloxy, free radical), 4-MeO-TEMPO (4-methoxy-2,2,6,6-tetramethylpiperidine-1-oxyl); 4-acetoamido-TEMPO (4-acetamido-2,2,6,6-tetramethylpiperidine-1-oxyl), and 4-hydroxy-TEMPO (4-hydroxy-2,2,6,6-tetramethylpiperidine-1-oxyl).

In some embodiments, the TEMPO catalyst is polymer-supported.

In some embodiments, the AZADO catalyst is chosen from 2-azaadamantane N-oxyl (AZADO), 1-methyl-2-azaadamantane-N-oxyl (1-Me-AZADO), and 9-azanoradamantane N-oxyl (Nor-AZADO).

In some embodiments, the nitroxyl radical catalyst is 9-azabicyclo[3.3.1]nonane N-oxyl (ABNO).

In some embodiments, the organic solvent is selected from acetonitrile, tetrahydrofuran, 2-methyltetrahydrofuran, diethyl ether, methyl tert-butyl ether, dimethoxyethane, 2-methoxyethyl ether (diglyme), triethylene glycol dimethyl ether (triglyme), toluene, benzene, hexane, pentane, dioxane, and mixtures thereof.

In some embodiments, the organic solvent is acetonitrile.

In some embodiments, the phosphate buffer comprises an aqueous solution of potassium phosphate monobasic and potassium phosphate dibasic.

In some embodiments, the potassium phosphate monobasic and potassium phosphate dibasic are each used in amounts of about 0.5 equivalent to about 1.5 equivalents. In some embodiments, the potassium phosphate monobasic and potassium phosphate dibasic are each used in amounts of about 1.1 equivalents to about 1.5 equivalents.

In some embodiments, the amount of the nitroxyl radical catalyst used is about 1.0 to about 50.0 mol percent. In some embodiments, the amount of the nitroxyl radical catalyst used is about 1.0 to about 10.0 mol percent. In some embodiments, the amount of the nitroxyl radical catalyst used is about 5.0 to about 10.0 mol percent. In some embodiments, the amount of the nitroxyl radical catalyst used is about 7.0 mol percent.

In some embodiments, the amount of sodium chlorite used is about 1 equivalent to about 3 equivalents. In some embodiments, the amount of sodium chlorite used is about 1.5 equivalent to about 2 equivalents. In some embodiments, the amount of sodium chlorite used is about 1.7 equivalents.

In some embodiments, the sodium sulfite is aqueous sodium sulfite.

In some embodiments, the sodium sulfite is solid sodium sulfite.

In some embodiments, the amount of sodium sulfite used is about 1 to about 3 equivalents. In some embodiments, the amount of sodium sulfite used is about 2.4 to 2.5 equivalents.

Also provided is 4-phenyl-1-butyric acid prepared by a process described herein.

In some embodiments, the 4-phenyl-1-butyric acid prepared by a process described herein does not require further purification.

In some embodiments, the process further comprises adding aqueous HCl to the quenched reaction to adjust the pH to about pH 3; and collecting the 4-phenyl-1-butyric acid by filtration.

In some embodiments, the process further comprises adding aqueous HCl to the quenched reaction to adjust the pH to about pH 6.5; adding a seed crystal of 4-phenyl-1-butyric acid; and collecting the formed 4-phenyl-1-butyric acid by filtration.

In some embodiments, the 4-phenyl-1-butyric acid prepared by a process described herein is greater than about 80% pure by weight. In some embodiments, the 4-phenyl-1-butyric acid prepared by a process described herein is greater than about 85% pure by weight. In some embodiments, the 4-phenyl-1-butyric acid prepared by a process described herein is greater than about 90% pure by weight. In some embodiments, the 4-phenyl-1-butyric acid prepared by a process described herein is greater than about 93% pure by weight.

In some embodiments, the 4-phenyl-1-butyric acid prepared by a process described herein is greater than about 80% pure by high performance liquid chromatography (HPLC) analysis. In some embodiments, the 4-phenyl-1-butyric acid prepared by a process described herein is greater than about 85% pure by high performance liquid chromatography (HPLC) analysis. In some embodiments, the 4-phenyl-1-butyric acid prepared by a process described herein is greater than about 90% pure by high performance liquid chromatography (HPLC) analysis. In some embodiments, the 4-phenyl-1-butyric acid prepared by a process described herein is greater than about 95% pure by high performance liquid chromatography (HPLC) analysis. In some embodiments, the 4-phenyl-1-butyric acid prepared by a process described herein is greater than about 97% pure by high performance liquid chromatography (HPLC) analysis. In some embodiments, the 4-phenyl-1-butyric acid prepared by a process described herein is greater than about 98% pure by high performance liquid chromatography (HPLC) analysis. In some embodiments, the 4-phenyl-1-butyric acid prepared by a process described herein is greater than about 99% pure by high performance liquid chromatography (HPLC) analysis.

In some embodiments, the process further comprises purifying the 4-phenyl-1-butyric acid.

Also provided is a process for converting 4-phenyl-1-butyric acid prepared as described herein to glycerol triphenylbutyrate comprising esterifying glycerol with three molecules of 4-phenyl-1-butyric acid. In some embodiments the process for converting 4-phenyl-1-butyric acid prepared as described herein to glycerol triphenylbutyrate comprises: converting 4-phenyl-1-butyric acid prepared by the process disclosed herein to 4-phenyl-1-butyryl chloride; and reacting the 4-phenyl-1-butyryl chloride with glycerol in an organic solvent in the presence of a suitable base.

4-Phenyl-1-butyric acid may be conveniently converted to the corresponding acid chloride by any of the means known to those skilled in the art of synthesis. In some embodiments, the conversion of 4-phenyl-1-butyric acid or a salt thereof to the acid chloride is done by reacting 4-phenyl-1-butyric acid or a salt thereof with thionyl chloride.

In some embodiments, the base for the reaction of 4-phenyl-1-butyryl chloride with glycerol is selected from triethylamine, imidazole, 1-methylimidazole, and 1-ethylimidazole.

In some embodiments, the solvent for the reaction of 4-phenyl-1-butyryl chloride with glycerol is selected from tetrahydrofuran, dichloromethane, chloroform, carbon tetrachloride, and ethylenedichloride.

Also provided is glycerol triphenylbutyrate prepared by a process described herein.

Also provided is a pharmaceutical composition comprising glycerol triphenylbutyrate prepared by a process described herein. In some embodiments the pharmaceutical composition does not include any pharmaceutically acceptable excipients. In some embodiments the pharmaceutical composition comprises one or more pharmaceutically acceptable excipients.

Also provided is a method for treating a subject with a nitrogen retention disorder comprising administering to the subject glycerol triphenylbutyrate prepared by a process described herein.

In some embodiments, the nitrogen retention disorder is selected from urea cycle disorders and hepatic encephalopathy. In some embodiments, the nitrogen retention disorder is a urea cycle disorder.

In some embodiments, the subject to be treated is a human patient. In some embodiments, the human patient is an adult. In some embodiments, the human patient is a pediatric subject 12 to 18 years of age. In some embodiments, the human patient is a pediatric subject under the age of 12.

In some embodiments, the glycerol triphenylbutyrate is administered orally. In some embodiments, the glycerol triphenylbutyrate is administered directly into the mouth via oral syringe or dosing cup. In some embodiments, the glycerol triphenylbutyrate is administered by nasogastric tube or gastrostomy-tube.

In some embodiments, the glycerol triphenylbutyrate is administered with food.

In some embodiments, the method for treating a subject with a urea cycle disorder comprises administering to the subject glycerol triphenylbutyrate prepared by a process described herein in a dosage of about 5.33 to 8.79 $g/m^2/day$. In some embodiments, the dosage is at or about 6 to 8 $g/m^2/day$, 6.5 to 7.5 $g/m^2/day$, 7.0 to 7.3 $g/m^2/day$, or 7.15 to 7.25 $g/m^2/day$. In some embodiments, the effective dosage is at or about 7.18 or 7.05 $g/m^2/day$.

The following examples serve to more fully describe the disclosed compounds the methods. It is understood that these examples in no way serve to limit the true scope of this invention, but rather are presented for illustrative purposes.

EXAMPLES

The following non-limiting examples are illustrative of certain embodiments of the present invention. The following abbreviations are used:

TEMPO: 2,2,6,6-tetramethyl-1-piperidinyloxy, free radical

MTBE: methyl tert-butyl ether

4-PBA: 4-phenyl-1-butyric acid

3-BPA: 3-benzoyl propionic acid

Example 1

Preparation of 4-phenyl-1-butyric acid

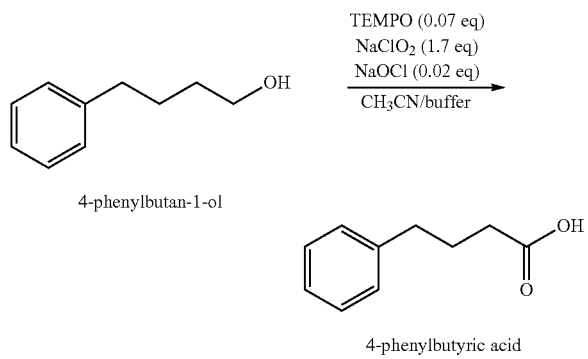

In a 50 L jacketed reactor, equipped with a Huber Unistadt 360 chiller, 4-phenyl-1-butanol (1 kg, 6.66 mol) and TEMPO (72.8 g, 466 mmol, 0.07 eq.) were dissolved in acetonitrile (5 L) at ambient temperature. In a 12 L 3-neck round bottom flask, a potassium phosphate buffer was prepared by dissolving potassium phosphate monobasic (996 g, 7.32 mol) and potassium phosphate dibasic (1276 g, 7.33 mol) in water (10 L), and the prepared buffer was transferred into the reaction mixture at ambient temperature. Two other solutions were prepared separately including an aqueous solution of sodium chlorite by dissolving sodium chlorite (1.28 kg, 11.32 mol, 1.7 eq.) in water (4 L) and bleach solution by diluting 8.25% bleach (110 mL, 122 mmol, 0.02 eq.) in water (200 mL). The temperature of the reaction mixture was adjusted to 10-40° C. followed by adding the prepared aqueous solution of sodium chlorite (900 mL) and the diluted bleach (60 mL) in sequence. The remaining of the two solutions was then slowly added simultaneously and separately over four hours while maintaining the temperature of the reaction mixture at 10-40° C. It was noted that after the addition, the temperature of the reaction mixture kept increasing to 30° C., and maintained at 30° C. for about two hours before starting to slowly cool down to 20° C. The mixture was agitated at 20° C. overnight, and the conversion was >99.9%. Temperature of the reaction mixture was adjusted to below 0-20° C. followed by pH adjustment to 9.8 with 25% aqueous sodium hydroxide (prepared from 50% aqueous sodium hydroxide with water, 1/1 v/v; ~1360 mL). An aqueous solution of sodium sulfite was prepared by dissolving sodium sulfite (2 kg, 15.87 mol, 2.4 eq.) in water (10 L), and slowly transferred into reaction mixture over one hour while maintaining the temperature at below 15° C. (note that the peak for 3-PBA increases to about 6-7 A % immediately after the sodium sulfite quench). The resulting light cloudy mixture was stirred at 15 to 30° C. overnight (to bring the levels of the 3-PBA peak back down to about 1.5 A %) and then cooled to 0-10° C. (to maximize precipitation of the inorganic salts). The suspension was stirred at 0-10° C. for two hours and then the solids removed by filtration through a Celite® pad (250 g). The filtered cake was washed with cold water (1 L×3). The combined filtrate was washed with MTBE (10+5 L). The resulting colorless aqueous phase was cooled to 0-10° C., and agitated overnight (no further precipitation of inorganic material was noted). It is essential to perform the acidification on a chilled solution, in order for the 4-PBA to precipitate. To the chilled solution was slowly added 6N aqueous HCl (1 L) over two hours to adjust pH to about 6.5. At this stage, 4-PBA seed (10 g, 60.9 mmol) was added to induce crystallization to form a thin suspension. Additional 6N aqueous HCl (2.6 L) was slowly added over two hours to adjust the pH to 3. The resulting suspension was agitated at 5° C. overnight, and then filtered to collect the solid. The wet cake was washed with ice cold water (2 L), and dried under vacuum with nitrogen purge to provide 4-PBA as white solid, which was dried in the open air, in glass trays over 3 days.

The total amount of the crude 4-PBA was 1034.1 g (94.6% isolation yield) with 99.7 A % purity by HPLC analysis, 210 nm and >99 A % by 260 nm (1 mg/mL acetonitrile solution). No 3-BPA was detected by both wavelengths. DSC analysis gave the melting point 52° C.

Next, the 4-PBA was analyzed by HPLC using with the concentration of 5 mg/mL in mobile phase A and acetonitrile (80/20 v/v). The purity was 99.7 A % with 93% w/w. Under this analysis 3-PBA was identified in 0.04 A % along with four other impurities in the range of 0.04 to 0.1 A %. The weight assay of 3-PBA was calculated as 0.002% w/w using 0.04% 3-BPA solution. Final Karl Fischer analysis was 0.14% w/w of water content.

Those skilled in the art will recognize that various modifications, additions, substitutions, and variations to the illustrative examples set forth herein can be made without departing from the spirit of the invention and are, therefore, considered within the scope of the invention.

We claim:

1. A process for preparing 4-phenyl-1-butyric acid, comprising:
reacting 4-phenyl-1-butanol with sodium chlorite, a nitroxyl radical catalyst and sodium hypochlorite in an organic solvent and a phosphate buffer; and quenching the reaction with sodium sulfite.

2. The process of claim 1, wherein said reacting 4-phenyl-1-butanol with sodium chlorite, the nitroxyl radical catalyst and sodium hypochlorite in an organic solvent and a phosphate buffer comprises sequentially adding sodium chlorite and sodium hypochlorite to a mixture of 4-phenyl-1-butanol and the nitroxyl radical catalyst in an organic solvent and a phosphate buffer.

3. The process of claim 1, wherein the nitroxyl radical catalyst is chosen from a TEMPO catalyst and an AZADO catalyst or a mixture thereof.

4. The process of claim 3, wherein the TEMPO catalyst is chosen from TEMPO (a free radical of 2,2,6,6-tetramethyl-1-piperidinyloxy), 4-MeO-TEMPO (4-methoxy-2,2,6,6-tetramethylpiperidine-1-oxyl); 4-acetoamido-TEMPO (4-acetamido-2,2,6,6-tetramethylpiperidine-1-oxyl), and 4-hydroxy-TEMPO (4-hydroxy-2,2,6,6-tetramethylpiperidine-1-oxyl).

5. The process of claim 3, wherein the TEMPO catalyst is polymer-supported.

6. The process of claim 3, wherein the AZADO catalyst is chosen from 2-azaadamantane N-oxyl (AZADO), 1-methyl-2-azaadamantane-N-oxyl (1-Me-AZADO), and 9-azanoradamantane N-oxyl (Nor-AZADO).

7. The process of claim 3, wherein the nitroxyl radical catalyst is 9-azabicyclo[3.3.1]nonane N-oxyl (ABNO).

8. The process of claim 1, wherein the organic solvent is selected from acetonitrile, tetrahydrofuran, 2-methyltetrahydrofuran, diethyl ether, methyl tert-butyl ether, dimethoxyethane, 2-methoxyethyl ether (diglyme), triethylene glycol dimethyl ether (triglyme), toluene, benzene, hexane, pentane, dioxane, and mixtures thereof.

9. The process of claim 8, wherein the organic solvent is acetonitrile.

10. The process of claim 1, wherein the phosphate buffer comprises an aqueous solution of potassium phosphate monobasic and potassium phosphate dibasic.

11. The process of claim 10, wherein potassium phosphate monobasic and potassium phosphate dibasic are each used in amounts of about 0.5 equivalent to about 1.5 equivalents.

12. The process of claim 1, wherein the amount of the nitroxyl radical catalyst used is about 1.0 to about 50.0 mol percent.

13. The process of claim 12, wherein the amount of the nitroxyl radical catalyst used is about 5.0 to 10.0 mol percent.

14. The process of claim 12, wherein the amount of the nitroxyl radical catalyst used is about 7.0 mol percent.

15. The process of claim 1, wherein the amount of sodium chlorite used is about 1 equivalent to about 3 equivalents.

16. The process of claim 15, wherein the amount of sodium chlorite used is about 1.5 equivalent to about 2 equivalents.

17. The process of claim 16, wherein the amount of sodium chlorite used is about 1.7 equivalents.

18. The process of claim 1, wherein the sodium sulfite is aqueous sodium sulfite.

19. The process of claim 1, wherein the sodium sulfite is solid sodium sulfite.

20. The process of claim 1, wherein the amount of sodium sulfite used is about 1 to about 3 equivalents.

* * * * *